United States Patent [19]

Jewell, Jr. et al.

[11] Patent Number: 4,650,890

[45] Date of Patent: Mar. 17, 1987

[54] PREPARATION OF OLEFINIC COMPOUNDS AND INTERMEDIATES THEREOF

[75] Inventors: Charles F. Jewell, Jr., Atlanta, Ga.; James R. Wareing, Randolph, N.J.

[73] Assignee: Sandoz corp., E. Hanover, N.J.

[21] Appl. No.: 759,536

[22] Filed: Jul. 26, 1985

Related U.S. Application Data

[63] Continuation-in-part of Ser. No. 596,411, Apr. 3, 1984, abandoned.

[51] Int. Cl.$^4$ .................. C07B 41/06; C07C 69/738; C07C 69/732; C07C 67/313
[52] U.S. Cl. ........................................ 556/446; 560/53; 560/57; 560/60; 560/174; 560/177; 560/183; 546/267; 546/268; 546/341; 546/342
[58] Field of Search ................. 556/446; 560/53, 177, 560/57, 174, 60, 183; 546/267, 268, 341, 342

[56] References Cited

U.S. PATENT DOCUMENTS 4,277,610  7/1981  Cohen et al. .................. 556/446

OTHER PUBLICATIONS

Streitwieser, et al "Introduction to Organic Chemistry" (1976) pp. 381–383, 394, 395.

*Primary Examiner*—Henry R. Jiles
*Assistant Examiner*—Dale A. Bjorkman
*Attorney, Agent, or Firm*—Gerald D. Sharkin; Richard E. Vila; Frederick H. Weinfeldt

[57] ABSTRACT

7-Substituted lower alkyl hept-6-enoates and 4-hydroxy-tetrahydropyran-2-ones bearing 6-olefinic substituents (E), (Z), ethyl erythro-3,5-dihydroxy-7-phenyl-hept-6-enates are prepared by a multi-step process involving lower alkyl 3,5-dihydroxy-hept-6-enates. The final products are useful as anti hypercholesteremic agents.

15 Claims, No Drawings

PREPARATION OF OLEFINIC COMPOUNDS AND INTERMEDIATES THEREOF

This is a continuation-in-part of pending application Ser. No. 596,411 (filed Apr. 3, 1984), abandoned.

This invention relates to a process for preparing organic compounds, and more specifically for preparing hydroxy-tetrahydropyran-2-ones having 6-olefinic substituents and 7-substituted hept-6-enoic acid derivatives, as well as intermediates, per se in the process.

This invention provides a novel process for the preparation of trans olefins of the formula I:

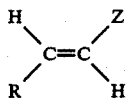
I wherein R is: a phenyl structure of formula A:

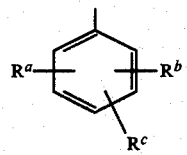
A in which
each of the $R^a$, $R^b$ and $R^c$ is independently hydrogen; halogen; $C_{1-4}$ alkyl; $C_{1-4}$ haloalkyl; phenyl; or phenyl substituted by halogen; $C_{1-4}$ alkoxy; $C_{2-8}$ alkanoyloxy; $C_{1-4}$ alkyl or $C_{1-4}$ haloalkyl; or $OR^d$ in which $R^d$ is any of hydrogen, $C_{2-8}$ alkanoyl, benzoyl, phenyl, halophenyl, phenyl $C_{1-3}$ alkyl, $C_{1-9}$ alkyl, cinnamyl, $C_{1-4}$ haloalkyl, allyl, cycloalkyl-$C_{1-3}$-alkyl, adamantyl-$C_{1-3}$-alkyl, or substituted phenyl-$C_{1-3}$-alkyl in each of which the substituents are selected from the group consisting of halogen, $C_{1-4}$ alkoxy, $C_{1-4}$ alkyl, or $C_{1-4}$ haloalkyl;
a naphthyl or tetrahydronaphthyl structure of the formula B:

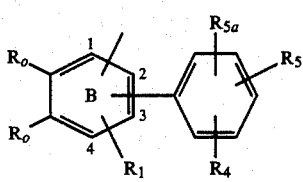
B wherein the two $R_o$ groups together form a radical of the formula

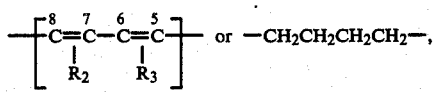
or —CH$_2$CH$_2$CH$_2$CH$_2$—, or —CH$_2$CH$_2$CH$_2$CH$_2$—,
wherein
$R_2$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy;
$R_3$ is hydrogen, $C_{1-3}$alkyl, $C_{1-3}$alkoxy, trifluoromethyl, fluoro, chloro, phenoxy or benzyloxy; with the provisos that not more than one of $R_2$ and $R_3$ is trifluoromethyl, not more than one of $R_2$ and $R_3$ is phenoxy, and not more than one of $R_2$ and $R_3$ is benzyloxy;
$R_1$ is hydrogn, $C_{1-6}$alkyl not containing an asymmetric carbon atom, fluoro, chloro or benzyloxy;
$R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy;
$R_5$ is hydrogen, $C_{1-3}$alkyl, $C_{1-3}$alkoxy, trifluoromethyl, fluoro, chloro, phenoxy or benzyloxy;
$R_{5a}$ is hydrogen, $C_{1-2}$alkyl, $C_{1-2}$alkoxy, fluoro or chloro;
with the provisos that not more than one of $R_4$ and $R_5$ is trifluoromethyl, not more than one of $R_4$ and $R_5$ is phenoxy, and not more than one of $R_4$ and $R_5$ is benzyloxy; with the proviso that on ring B the free valence and ring A are ortho- to each other; or
an indol-type radical of the formula C:

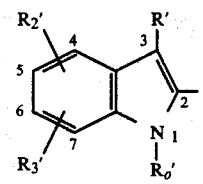
C wherein one of $R'$ and $R_o'$ is

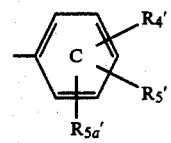

and the other is primary or secondary $C_{1-6}$alkyl not containing an asymmetric carbon atom, $C_{3-6}$cycloalkyl or phenyl(CH$_2$)$_m$—,
wherein
$R_4'$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy;
$R_5'$ is hydrogen, $C_{1-3}$alkyl, $C_{1-3}$alkoxy, trifluoromethyl, fluoro, chloro, phenoxy or benzyloxy;
$R_{5a}'$ is hydrogen, $C_{1-2}$alkyl, $C_{1-2}$alkoxy, fluoro or chloro; and m is 1, 2 or 3;
with the provisos that both $R_5'$ and $R_{5a}'$ must be hydrogen when $R_4'$ is hydrogen; $R_{5a}'$ must be hydrogen when $R_5'$ is hydrogen; not more than one of $R_4'$ and $R_5'$ is trifluoromethyl; not more than one of $R_4'$ and $R_5'$ is phenoxy and not more than one of $R_4'$ and $R_5'$ is benzyloxy;
$R_2'$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy;
$R_3'$ is hydrogen, $C_{1-3}$alkyl, $C_{1-3}$alkoxy, trifluoromethyl, fluoro, chloro, phenoxy or benzyloxy; with the provisos that $R_3'$ must be hydrogen when $R_2'$ is hydrogen; not more than one of $R_2'$ and $R_3'$ is trifluoromethyl; not more than one of $R_2'$ and $R_3'$ is phenoxy; and not more than one of $R_2$ and $R_3$ is benzyloxy; and
Z is

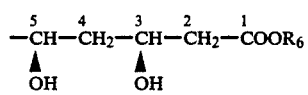

(II)

or

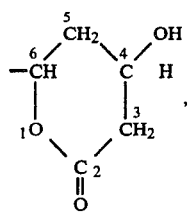

(III)

wherein $R_6$ is hydrogen, $C_{1-3}$alkyl, n-butyl, i-butyl, t-butyl and benzyl; or M;

wherein M is a pharmaceutically acceptable cation

The compounds of formula I constitute 3 classes of compounds depending on the nature of R, namely (1) compounds IA, where R is of formula A, IB where R is of formula B, and of IC when R is of formula C. Within the main classes, subclass can be seen, such as type IB-1 where $R_o+R_o$ is an alkadienyl chain and type IB-2 where $R_o+R_o$ is a alkylene chain; types IC-1 and IC-2 depending upon whether Ring C is at position-1 or -3.

Preferred compounds I are those in which (1) when Z is of type II the alcohol oxygens have the erythro relationship and (2) when Z is of type III the alcohol oxygen at the carbon-3 and the substituent at carbon-6 are trans to each other.

Compounds IA are known and described in U.S. Pat. No. 4,308,378 (issued Dec. 29, 1981) and European Patent No. 11,928 (published June 11, 1980) wherein the compounds are disclosed to be useful as anti-hypercholesteremic agents. Compounds IB are disclosed in PCT Application WO 84/02903 (published Aug. 2, 1984) and pending application No. 570,584 filed on Jan. 13, 1984. Compounds IC are disclosed in PCT Application WO 84/02131 (published June 7, 1984) and pending application No. 722,288 filed Nov. 11, 1984. Compounds IB and IC are useful as anti-hypercholesteremic agents as they are inhibitors of cholesterol biosynthesis in the manner of the known products compactin and mevinolin and are therefore useful in the treatment of atherosclerosis, as described in said applications.

The terms "halogen" and "halo" as used in the definition of compounds IA is intended to include fluoro and chloro.

An embodiment of this invention is multi-step process for the preparation of compounds I, which process may conveniently be represented by Reaction Scheme A, below, wherein R is as defined above. $R_6'$ is the same as $R_6$ when it is not hydrogen or,; and $p^1$ is a protecting (or masking) group for a hydroxy function; and $R_7$ and $R_8$ are, independently, hydrogen or alkyl, e.g. having from 1 to 6 carbon atoms, such as methyl; preferably at least one of $R_7$ and $R_8$ is hydrogen, and more preferably both $R_7$ and $R_8$ are hydrogen. The final products I are shown as compounds I' where A is of type II and $R_6$ and $R_6'$; I" where $R_6$=H or M, and I where Z is of type III. The reactant J is an α,β-unsaturated aldehyde, such as acrolein.

REACTION SCHEME A

A

↓ addition process (a)

J  CH=C—R₇
   |    |
   HC   R₈
   ‖
   O

B  (structure with OH, and two C=O groups, OR₆')
   H—C
      ‖
      C
     / \
   R₇   R₈

↓ Reduction process (b)

C  (structure with OH, OH, C=O OR₆')
   H—C
      ‖
      C
     / \
   R₇   R₈

↓ protective etherification process (c)

D  (structure with OP¹, OP¹, C=O OR₆')
   H—C
      ‖
      C
     / \
   R₇   R₈

↓ O₃ oxidation process (d)

E  (structure with OP¹, OP¹, C=O OR₆')
   H
   |
   O=C

↓ Wittig Reax. process (e)

F  (structure with OP¹, OP¹, C=O OR₆')
   H—C
      ‖
   R—C—H

↓ deprotection process (f)

I' (structure with OH, OH, C=O OR₆')
   H—C
      ‖
   R—C—H process (g) ↙       ↘ process (i)

I"  ——process (h)——→  I'"

The process steps of Reaction Scheme A are discussed individually below.

In process (a) the olefinic-bearing intermediate B is prepared. Process (a) may be accomplished in three steps. First, an alkali metal salt of the starting material A (an ester of acetoacetic acid) is formed by treating with an alkali metal-source, e.g. a hydride, such as sodium hydride, in an inert medium, e.g. a cyclic ether, such as tetrahydrofuran (THF), at reduced temperatures, e.g. 0° to 10° C., under essentially anhydrous conditions; thus yielding a salt of the formula A':

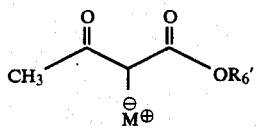

wherein $R_6'$ is as defined above, and M is an equivalent of an alkali metal.

Such alkali metal salts are preferably used for the second part of process (a) in situ, thus utilizing the same medium. The second part of process (a) is carried out also at reduced temperatures and still under anhydrous conditions e.g. about 10° C., a strong lithium base, e.g. a lithium hydrocarbon reagent, such as butyl lithium, in a dry medium, e.g. hexane, is added to the alkali metal salt to form a dianion of the formula A'':

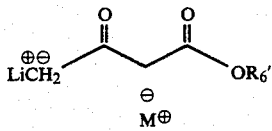

wherein M and $R_6'$ are as defined above.

In the third step, a compound J is introduced at about −30° C., stirred, and then the temperature allowed to rise. Any unreacted metallic reagents are first decomposed by adding water, then the reaction product, B is recovered. If desired, a compound A'' may be prepared in one step by reacting a compound A with at least two equivalents of a strong lithium base, such as lithium diisoproplamide, the other conditions being the same.

In process (b), the keto group of the ketoester of Formula B is reduced to a hydroxy group with a mild reducing agent such as sodium borohydride or a complex of t-butylamine and borane in an inert organic solvent such as a lower alkanol, preferably ethanol, conveniently at a temperature of −10°−−30° C., utilizing at least 1, for example 2-4, equivalents of transferable hydride per mole of compound of Formula B, under an inert atmosphere. The reaction time is suitably 1-8 hours. The dihydroxyesters of Formula C exist in four stereoisomeric forms; however, if an optically pure starting material of Formula B is utilized, only two optical isomers (diastereoisomers) of the resulting dihydroxyester of Formula C are obtained.

However, it is preferred to utilize a stereoselective reducing agent in process (b) to maximize production of the erythro stereoisomers (racemate) of which the preferred stereoisomer (as set forth above) is a constituent. Process b is preferably carried out in three steps. In the first step, the ketoester of Formula B is treated with a tri-(primary or secondary $C_{2-4}$alkyl)borane, preferably tri-n-butylborane, (optionally adding air) to form a complex. The molar ratio of the tri-n-butylborane to the ketoester of Formula B is preferably 1-1.2:1, more preferably 1.1:1, and if desired 2-8 liters, preferably 4-6.5 liters of air (at 25° C. and 760 mm Hg) per mole of the ketoester are used. In the first step of process (b) the reaction temperature is suitably 0°-50° C., preferably 20°-30° C., and the reaction time is suitably 1-6 hours, preferably 1.5-2.5 hours. This reaction is carried out in an anhydrous inert organic solvent, preferably an ether solvent such as tetrahydrofuran, diethyl ether, 1,2-dimethoxyethane or 1,2-diethoxyethane, with tetrahydrofuran being the most preferred solvent. Preferably the resulting complex is retained in situ.

In the second step, the complex is reduced with sodium borohydride, preferably in the same solvent as utilized for the first step, at from about −90° C. to −40° C., preferably −90° to −70° C. Preferably, 0.4-1.2, more preferably 0.4-1 mole of sodium borohydride per mole of the ketoester of Formula B are utilized. Any unreacted reducing agent is then decomposed, e.g. by adding dilute hydrochloric acid, and the product recovered for use in the third step.

In the third step, the product of the second step is treated with aqueous, e.g., 30%, hydrogen peroxide, an aqueous buffer preferably a phosphate buffer, having a pH of 7.0-7.2 (e.g., a 0.047M sodium phosphate 0.024M potassium phosphate/0.054M sodium hydroxide buffer) and a lower alkanol, preferably methanol, to obtain the dihydroxyester of Formula C. A large molar excess of hydrogen peroxide, e.g., 30-100, more typically 50-70, moles per mole of the ketoester of Formula B is employed. Thus, when 30% aqueous hydrogen peroxide is employed, 2.6-8.6 liters, more typically 4.3-6.0 liters, preferably 5.5-5.8 liters, per mole of the ketoester of Formula B are usually employed. Sufficient buffer to maintain the desired pH (7.0-7.2) should be utilized; when 30% aqueous hydrogen peroxide and the aforementioned phosphate buffer are utilized, 2 liters of said buffer per liter of 30% aqueous hydrogen peroxide are used. As for the lower alkanol, it is preferable to employ 1-3 liters, more preferably 2 liters, per liter of 30% aqueous hydrogen peroxide. The third step is carried out by slowly adding a solution of the hydrogen peroxide, buffer and lower alkanol to the reaction mixture obtained from the second step, stirred at −80°−−40° C., preferably −80°−−70° C., allowing the reaction mixture to warm to 20°-30° C.

In process (c), a compound C is converted to a corresponding compound D by conversion of the two hydroxy functions to protected forms. Process (c) may be accomplished by reacting a compound C with at least 2 equivalents thereof of a protecting group-bearing reagent of the formula IV:

$$P^1\text{—}L \qquad \qquad IV$$

in which $P^1$ is as defined above and L is a leaving group, in the presence of an acid acceptor, e.g., imidazol, in an inert medium, e.g., a liquid amide, such as dimethyl formamide (DMF) at moderate temperatures, e.g., from about 5° to 40°, under essentially anhydrous conditions. Leaving groups are well known in the art, and include higher halo, i.e., chloro, bromo, or iodo, preferably chloro, and alkyl and aryl sulfonyl, radicals, e.g., $C_1$-$C_6$ alkyl or phenyl which may be unsubstituted or monosubstituted by a $C_1$-$C_4$ alkyl, such as p-toluene sulphonyl.

Suitable protective groups $P^1$, include tri-substituted silyl radicals having at least 2, and preferably 3 bulky radicals, i.e. radicals selected from the group consisting of (a) tertiary alkyl ($C_4$ to $C_8$) groups especially t-butyl, and (b) aryl, preferably phenyl which may be unsubstituted or substituted by up to 2 (preferably 0 or 1) of any of lower alkyl (C$_1$-C$_4$), chloro, nitro, trifluoromethyl, or mono-substituted in the para-position by phenyl or benzyl (which may be unsubstituted or in turn substituted by one or two of such groups as mentioned above, especially at the para-position) and the remaining substituent, where present, is a non-bulky radical, eg unbranched alkyl having from 1 to 4 carbon atoms, eg methyl.

A preferred P$^1$ is the diphenyl tertiarybutylsilyl radical and a preferred compound IV is chlorodiphenyl t-butylsilane. Alternatively, P$^1$ may be lower alkyl, e.g. having from 1 to 4 carbon atoms, such as methyl.

In process (d) compounds D are converted to corresponding compounds E by oxidation of the vinyl group to an aldehedic function. The oxidation may be obtained by conventional means for oxidizing an olefinic position to a carbonyl function. A particularly convenient method of carrying out process (d) is by treating a compound D in an inert medium e.g. a chlorinated hydrocarbon, such as methylenechloride, methanol or ethyl acetate, with ozone at reduced temperatures, e.g. at from about $-50°$ to $-80°$ C. e.g. about $-78°$ C. When the required amount of ozone has been reacted, the intermediate ozonide is decomposed by the addition of a mild reducing agent, such as dimethyl sulfide or triphenylphosphine to the reaction mixture to yield the desired aldehyde; a preferred method being use of ethylacetate and triphenylphosphine Final steps in the process are the reaction (process e) of the protected di-hydroxy aldehyde (E) with a Wittig reagent bearing the desired R-moiety (a compound X$^o$) to give a protected di-hydroxy form of a final product (F), which is then deprotected (process f) to yield a desired final product (I) which may then be converted to final compounds I" or I''' as desired.

In process (e) Wittig reagents have the formula X$^o$:

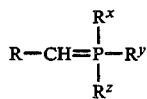   X$^o$ wherein R is as defined above and each of R$^x$, R$^y$ and R$^z$ is, independently, an aryl or alkoxy (C$_1$-C$_6$) radical. Process (e) is conveniently carried out in an inert medium, e.g., a cyclic ether such as tetrahydrofuran at reduced temperatures, e.g. $-15°$ to $+5°$ C., such as $-10°$ to $0°$ C. under essentially anhydrous conditions.

The Wittig reagents X$^o$ are prepared by treating a compound of formula X:

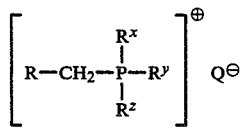   X in which R, R$^x$, R$^y$, R$^z$ are as defined above, and Q is a higher halo (having an atomic weight of from about 34 to 120), e.g., chloro, bromo or iodo, with a strong base, such as an alkali metal salt of a hydrocarbon, e.g., n-butyl lithium, in an inert medium, such as a cyclic ether, at reduced temperatures, e.g., from about $-15°$ to $0°$ C., e.g., about $-10°$ C. Conveniently the Wittig reagent is used in situ, so that the conditions and medium employed in its preparation are also utilized in its reaction with a compound E, i.e. in process (e).

In the Wittig reagents, when any of R$^z$, R$^x$ or R$^y$ is aryl, it is preferably phenyl which is unsubstituted or substituted by one or two lower alkyl (C$_1$-C$_4$) or chloro substituents; when any is alkoxy, it is preferably ethoxy. Preferably R$^x$, R$^y$ and R$^z$ are the same.

The above-mentioned compounds of formula X are obtainable in the conventional method for preparing such reagents; a convenient method is by reacting a compound of the formula X':

R—CH$_2$—Q     X' in which R and Q are as defined above, with a phosphine of the formula X":

   X"

in which R$^x$, R$^y$ and R$^z$ are as defined above, e.g. triphenyl phosphine, in an inert anhydrous organic solvent, for example a hydrocarbon such as benzene, toluene or xylene, or a mixture thereof, at a ratio of about 1-1.1 moles of phosphine (X") per mole of halide (X'). The reaction temperature is conveniently 60° C. to reflux, preferably not in excess of 150° C., and, while the reaction time is inversely related to the reaction temperature, it is conveniently 2-8 hours. The reaction is run under essentially anhydrous conditions, e.g. in an inert atmosphere.

Compounds X' are obtainable by halogenating a corresponding alcohol of the formula X''':

R—CH$_2$—OH     X''' in which R is as defined. The halogenation may be carried out in the conventional manner. Compounds X''', in turn are obtainable by reducing esters of formula X$^{IV}$:

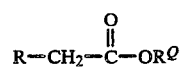   X$^{IV}$ in which R is as defined above and R$^Q$ is methyl or ethyl preferably methyl. Compounds X$^o$ are conveniently prepared by the method disclosed in Application Nos. 722,288 (filed Nov. 11, 1984) and 570,584 (filed Jan. 13, 1984), noted above; said applications being incorporated by reference herein.

In process (f) the deprotection of a compound F to its corresponding compound I', may be accomplished in the conventional manner. Where the protecting group is a silyl-type, then fluoride or acid treatment is employed, e.g., using a mixture of at least equal (e.g. 2 times) molar portions of acetic acid and tetrabutylammonium fluoride (TBAF) in THF, methanolic HCl, or fluoride anion reagents. Moderate temperatures may be employed, e.g., from about 20° to 60°, e.g., 20° to 30° C. When P$^1$ is alkyl, then deprotection may be accomplished by treatment with BBr$_3$ in methylenechloride at about $-23°$ C.

In process (g) a compound I', i.e. the deprotected form of a compound F, is saponified. This is achieved by treatment with aqueous alkali metal base, e.g., sodium hydroxide, preferably in a water-miscible co-solvent, e.g. dioxane, at reduced temperatures, e.g. from about −5° to +10° C., such as in an ice bath. Where a product is desired in which $R_6$ is hydrogen, i.e., the free acid form, such is obtained by acidifying the salt form (where $R_6$=M) by conventional means, e.g., by addition of dilute hydrochloric acid.

Process (h) is accomplished by heating a compound I″ in which $R_6$=H, in an inert medium, e.g. an aromatic hydrocarbon such as toluene at from about 80° to 140° C., for example at the reflux temperature of the reaction medium.

Alternatively, a compound I′ may be directly converted to its corresponding compound I‴ by carrying out the procedure of process (f) and heating, e.g. at about 80° to 140°, e.g. at the refluxing temperature of the reaction medium, i.e. process (i).

Reagents and starting materials described herein, e.g., compounds A, X″ and $X^{IV}$ are known and obtainable by known means, or where not known, may be obtained by adaptation of methods reported in the literature for the preparation of known analogs; some compounds being commercially available.

The final products and intermediate compounds described herein may be recovered and refined, where such is desired, by conventional means, such as by crystallization, distillation or chromatographic techniques such as column or thin layer chromatography, e.g., silica gel column chromatography.

The following examples are illustrative of the invention. All temperatures are centigrade and room temperature is 20° to 30° C., unless indicated otherwise.

Evaporations are done under vacuum employing minimal heating. Drying of organic phases is done over anhydrous sodium sulfate, unless indicated otherwise.

Where NMR characterization data is presented, the analysis is run in $CDCl_3$ and values given in ppm; digits in parenthesis are number of protons; and t=triplet, d=doublet, s=singlet, m=multiple and b is broad, J is coupling factor, unless indicated otherwise, and q is quartet.

Processes (f) to (i) do not form part of this invention.

EXAMPLE 1

Ethyl erythro-3,5-(diphenyl-t-butylsiloxy)-6-oxohexanoate (a compound E).

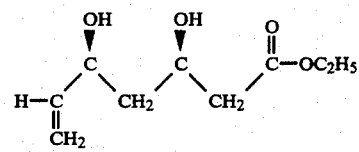

Step A, ethyl 5-hydroxy-3-oxo-hept-6-enoate (a compounc B)

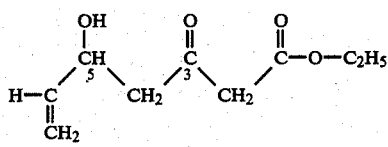

2.4 g of hexane-washed sodium hydride is suspended in 150 ml of dry tetrahydrofuran at 0° C., and 13 g of ethyl acetoacetate in 20 ml dry tetrahydrofuran is added dropwise. Gas elution stops after stirring at 0° to 10° C. for ½ hour. 76.9 ml of a 1.3 molar solution of butyl lithium in dry hexane is added while maintaining the temperature below 10° C. The resulting yellow solution is cooled to −30° C. and 5.6 g of acrolein in 10 ml tetrahydrofuran is added maintaining the temperature below −30° C. The resulting green solution is stirred ½ hour at −30° C. and then allowed to warm to room temperature over 2 hours. After adding 5 ml water, the tetrahydrofuran is removed by evaporating and replaced with diethyl ether which is extracted 3 times with 50 ml portions of saturated brine, dried over anhydrous sodium sulfate, filtered and concentrated to obtain crude title product of this step as 18 g of a yellow oil, which is then refined by chromatography on silica gel, eluting with 1% ethyl acetate-methylene chloride to give 3.22 g of refined product as a light yellow liquid: 60 MHz NMR ($CDCl_3$) δ, 5.5–6.1 (m, 1H), 4.8–5.4 (m, 2H), 4.3–4.6 (m, 1H), 4.08 (q, 2H), 3.39 (s, 2H), 2.67 (d(J=6 Hz 2H), 2.15 (s, 1H), 1.18 (t, 3H).

Step B, ethyl erythro-3,5-dihydroxy-hept-6-enoate (a compound C)

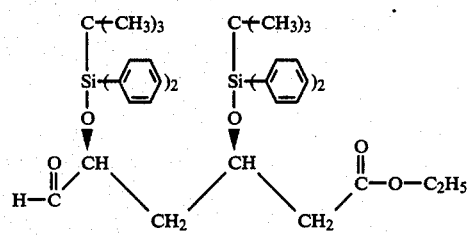

To 3 g of ethyl 5-hydroxy-3-oxo-hept-6-eneoate obtained by Step A above, dissolved in 50 ml dry tetrahydrofuran is added 20 ml of a 1 molar solution of tributyl(boron) in tetrahydrofuran. After 2 hours at room temperature the solution is cooled to −86° C., and 0.756 g of solid powdered sodium borohydride is added. Stirring is continued at −86° C. for 46 hours. Dilute hydrochloric acid (10%) is then added until foaming stops and the mixture is allowed to warm to room temperature, poured into 200 ml of saturated brine and extracted three times with diethyl ether. The diethyl ether extracts are combined and evaporated to a residue which is taken up in 250 ml methanol. 125 ml of pH 7 phosphate buffer (J. T. Baker Chemical Co.) and 100 ml of 30% hydrogen peroxide are added. After 3 hours at room temperature, the methanol is removed by evaporating, 300 ml saturated brine is added and the mixture extracted four times with 50 ml portions of diethyl ether. The combined ether extracts are washed three times with saturated sodium thiosulfate (aq.), then with brine and then dried, and concentrated to give 2.15 g of the title product of this step as a light yellow liquid: 200 MHz NMR ($CDCl_3$) 5.8–6.0 (m, 1H), 5.1–5.4 (m, 2H), 4.37–4.50 (m, 1H), 4.25–4.37 (m, 1H), 4.2 (q, 2H), 3.72 (bs, 1H), 3.15 (bs, 1H), 2.52 (d(J=7 Hz), 2H), 1.6–1.8 (m, 2H), 1.3(t, 3H).

Step C, ethyl erythro-3,5-di-(diphenyl t-butylsiloxy)-hept-6-enoate (a compound D).

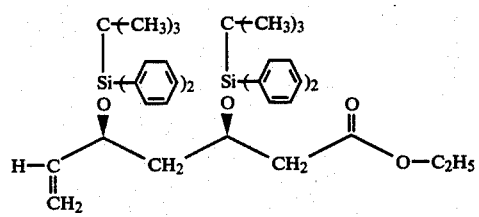

300 mg of ethyl erythro-3,5-dihydroxy-hept-6-enoate (obtained by Step B, above) and 869.1 mg of imidazole dissolved in 16 ml of dry dimethylformamide is stirred at room temperature under a nitrogen atmosphere, while 1.66 ml of tert-butyl diphenylsilyl chloride is added. The mixture is stirred overnight, poured into saturated brine (150 ml) and extracted three times with 150 ml portions of diethyl ether. The combined ether extracts are washed three times with cold dilute hydrochloric acid (5%) followed by saturated aq. sodium bicarbonate, then saturated brine, dried over anhydrous magnesium sulfate, filtered and concentrated to 1.945 g of crude product of this step as an oil which can be "flash" chromatographed on silica gel, eluting with 35% methylene chloride in hexane to yield 285 mg of the title product of this Step as a colorless oil: 200 MHz NMR (CDCl$_3$) δ 7.2–7.7 (m, 20H), 5.3–5.5 (m, 1H), 4.55–4.75 (m, 2H), 4.1–4.3 (m, 2H), 3.9–4.1 (m, 2H), 2.15–2.5 (m, 2H), 1.6–1.9 (m, 2H), 1.15 (t J=7 Hz)3H) 0.98 (s, 9H), 0.92 (s, 9H) IR (neat) C=O), 1734 cm$^{-1}$.

Step D, ethyl erythro-3,5-(diphenyl-t butylsiloxy)-6-oxo-hexanoate.

175.2 mg of ethyl erythro-3,5-di-diphenyl(tert-butyl-silyloxy)-hept-6-enoate (obtained by Step D above) dissolved in 26 ml methylene chloride and cooled to −78° C., is treated with a stream of ozone introduced below the surface of the solution, generated externally via a Welsbach Ozonator, for five minutes at which time a blue tint develops in the reaction flask and the ozone stream is terminated. One ml of dimethyl sulfide is added to the reaction mixture and the temperature is allowed to rise to room temperature. Concentration gives crude product of this step as an oil which is refined by chromatographing on silica and eluting with diethyl ether-hexane (1:3) to give refined title product of this step as 127.2 mg of a colorless oil: IR (neat) 1736 (C=O) cm$^{-1}$; 200 MHz NMR (CDCl$_3$) 9.3 (s, 1H), 7.25–7.75 (m, 20H), 4.43 (m, 1H), 4.1 (m, 1H) 3.96 (q(J=7 Hz), 2H) 2.31 dd(J$_1$=6 Hz, J$_2$=2 Hz), 1.95(t(J=6 Hz), 2H), 1.14 (t(J=7 Hz), 3H), 1.05 (s, 9H), 0.98 (s, 9H).

Repeating the procedure of this example, but in Step A, in place of the ethyl acetoacetate used therein, using an approximately equivalent amount of methyl acetoacetate, there is accordingly obtained methyl erythro-3,5-(diphenyl (t-butylsiloxy)-6-oxo-hexanoate.

EXAMPLE 2

(E), (Z)-methyl erythro-3,5-dihydroxy-7-phenyl-hept-6-enoate (a compound I')

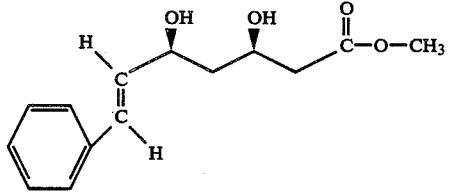

Step A,(E)-methyl erythro-3.5-di-(diphenyl-t-butyl-siloxy)-7-phenyl-hept-6-enoate (a compound F)

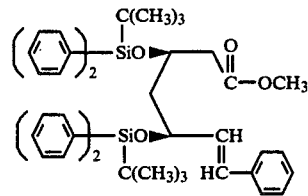

0.28 g (0.72 mmol) of benzyltriphenylphosphonium chloride is suspended in 2 ml of dry tetrahydrofuran (THF) and 0.4 ml of 1.55 M solution of n-butyl lithium (in THF) is added at −10°. The mixture is stirred at the reduced temperature for 40 minutes. To the resulting orange-colored solution, is added 0.47 g (0.72 mmol) of the methyl ester analogue of the title aldehyde product of Example 1 in 2 ml of dry THF. The resulting mixture is maintained at 0° for 18 hours, and then diluted with 50 ml methylene chloride, washed with water, the organic phase separated and dried and a residue obtained by evaporation.

The residue is chromatographed on silica using hexane: ethyl acetate (4:1) as eluant system to obtain 403 mg of the olefinic title product of this Example (as an oil) showing the following characteristics on analysis:

IR(CHCl$_3$): 3063, 3021, 2947, 2862, 1734 (ester CO), 1599, 1432, 1374, 1266, 1216, 1172, 1106, 829 and 780 cm$^{-1}$.

NMR (CDCl$_3$): 0.95 (s, 9H), 1.00(s, 9H), 1.78(m, 1H), 1.98(m, 1H), 2.38(dd, J$_1$=7 and J$_2$=15 Hz, 1H), 2.50 (dd, J$_1$=7, J$_2$=15 Hz, 1H), 3.52 (s, 3H), 4.33 (m, 2H), 5.80 (dd, J=16 Hz, 2H) and 6.98–7.70 (m, 25H) ppm.

Step B, (E),(Z)-methyl erythro-3,5-dihydroxy-7-phenylhept-6-enoate.

A solution of 455 mg (0.63 mmol) of the diprotected-olefinic product of Step A, above, 0.3 ml (5 mmol) of glacial acetic acid, and 5 ml (5 mmol) of 1M tetrabutylammonium fluoride (TBAF) solution in THF, is stirred at room temperature for 18 hours. The mixture is then diluted with 100 ml of methylene chloride, washed with water, the organic phase separated, dried, evaporated and the residue chromatographed on silica gel using ethyl acetate as eluant. The title product of this step is recovered as an oil having the following characteristics on analysis:

NMR (CDCl$_3$), 1.75 (m, 2H), 2.53 (m, 2H), 3.38 (b, 1H), 3.70 (s, 3H), 3.83 (b, 1H), 4.35 (br, 1H), 4.60 (b, 1H), 6.23 (dd, J$_1$=16, J$_2$=7 Hz, 1H), 6.69 (d, J=16 Hz, 1H) and 7.20–7.45 (m, 5H) ppm.

EXAMPLE 3

(E)-Trans-6-(2-phenylethenyl)-4-hydroxy-tetrahydropyran-2-one, (a compound I''').

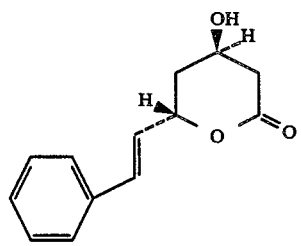

60 m.g. (0.24 mmol) of the dihydroxy ester product of Example 2 is dissolved in 1 ml of dioxane, and the solution cooled in an ice bath. 0.3 ml of 1N sodium hydroxide is then added. After 10 minutes the mixture is acidified (with dilute hydrochloric acid), and then extracted with two 10 ml portions of methylene chloride. The extract is taken to dryness by evaporating, and the resulting residue refluxed in toluene for 5 hours. The mixture is then evaporated and the resulting residue chromatographed on silica gel, eluting with ethyl acetate. The title product is recovered (43 mg) having a melting point of 94°–95°. Analysis shows the following characteristics for the product:

IR (CHCl$_3$): 3609, 3048, 2992, 2926, 1734, 1599, 1364, 1248, 1161, 1048 and 970 cm$^{-1}$.

NMR (CDCl$_3$). 1.62 (b, 1H), 1.95 (m, 1H), 2.13 (m, 1H), 2.68 (m, 1H), 2.83 (dd, J$_1$=17, J$_2$5 Hz, 1H), 4.45 (m, 1H), 5.38(m, 1H), 6.23 (dd, J=16 and 7 Hz, 1H), 6.73 (d, J=16 Hz, 1H) and 7.25–7.44 (m, 5H) ppm.

EXAMPLE 4

(E)-Sodium erythro-3,5-dihydroxy-7-(2′-[4″-fluorophenyl]naphth-1′-yl)hept-6-enoate

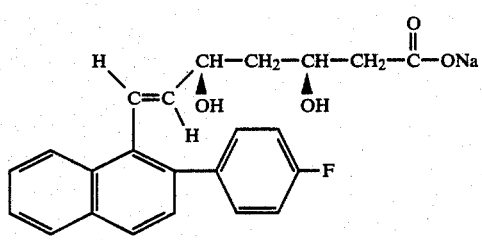

Step A (E)-Methyl erythro-3,5-di-(diphenyl-t-butylsiloxy)-7-(2′-[4″-fluorophenyl]naphth-1′-yl)hept-6-enoate (a compound I′).

Repeating the procedure of Step A of Example 2, but employing 555 mg (0.85 mmol) of the title aldehyde product of Example 1 and 450 mg (0.85 mmol) of 1-[2′-(4″-fluorophenyl)-naphth-1-yl]methyl triphenyl phosphonium chloride, and 0.55 ml of 1.55M butyllithium solution, there is obtained the title olefinic product of this step which is recovered by chromatography (430 mg) having the following characteristics on analysis:

IR (CHCl$_3$): 3055, 2949, 2864, 2350, 2334, 1736 (ester CO), 1601, 1506, 1469, 1435, 1374, 1247, 1197, 1163, 1108, 828, 800 and 672 cm$^{-1}$.

NMR (CDCl$_3$): 0.89 (s, 9H), 0.93 (s, 9H), 1.70 (m, 2H), 2.30, (m, 1H), 2.50 (m, 1H), 3.58 (s, 3H), 4.25 (m, 1H), 4.40 (m, 1H) 5.23 (dd, J=16 and 5 Hz, 1H), 6.31 (d, J=16 Hz, 1H), 6.88–7.90 (m, 30H) ppm.

Step B Sodium trans-3,5-dihydroxy-7-(2′-[4″-fluorophenyl]-napht-1′-yl)hept-6-enoate.

400 mg (0.47 mmol) of the di-protected olefinic product of Step A of this example is deprotected using tetrabutylammonium fluoride according to the procedure of Step B of Example 2, to obtain the corresponding Compound I′ (92 mg) which is treated with 1 equivalent of 1N sodium hydroxide solution in dioxane, the mixture washed with ether, and the aqueous phase is retained and on lyophilisation yields 88 mg of the product of this Example as an amorphous colorless solid, which upon analysis is characterized as follows:

IR (KBr): 1580 (COONa) cm$^{-1}$

NMR (D$_2$O): 1.20 (m, 1H), 1.45 (m, 1H), 2.13 (m, 2H), 3.55 (m, 1H), 4.13 (m, 1H), 5.23 (dd, J=16 and 6 Hz, 1H), 6.58 (d, J=16 Hz, 1H), and 6.85–8.00 (m, 10H) ppm.

EXAMPLE 5

(E)-Sodium erythro-7-[1′-methyl-3′-(4″-fluorophenyl)indol-2′-yl]-3,5-dihydroxyhept-6-enoate

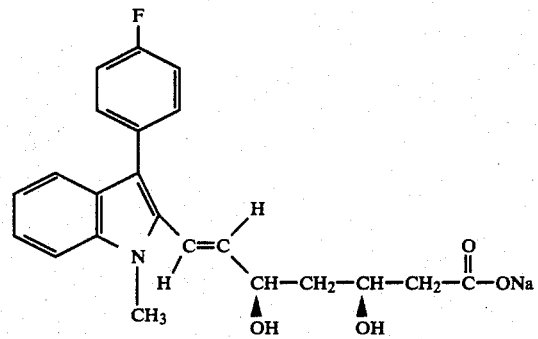

Step A, (E)-Methyl-erythro-7-[1′-methyl-3′-(4″-fluorophenyl)indol-2′-yl]-3,5 di-(diphenyl-t-butylsiloxy)hept-6-enoate.

Following the procedure of Step A of Example 2, but using 0.59 g (0.90 mmol) of the title aldehyde product (a compound E) of Example 1, and 482 mg (0.90 mmol) of [1′-methyl-3′-(4″-fluorophenyl)indol-2′-yl]methyltriphenyl phosphonium chloride, and treatment with a solution of butyl lithium the title di-protected olefinic ester of this step is obtained (366 mg) which upon analysis is characterized as follows:

NMR (CDCl$_3$): 0.85 (s, 9H), 0.95 (s, 9H), 1.75 (m, 2H), 2.38 (m, 1H), 2.55 (m, 1H), 3.33 (s, 3H), 3.53 (s, 3H), 4.23 (m, 1H), 4.35 (m, 1H), 5.45 (dd, J=16 and 6 Hz, 1H), 6.10 (d, J=16 Hz, 1H), 6.90–7.75 (m, 28H) ppm.

Step B, (E)-sodium erythro-7-[1′-methyl-3-(4″-fluorophenyl)indol-2′-yl]3,5-dihydroxyhept-6-enoate.

400 mg (0.49 mmol) of the di-protected ester obtained in Step A of this example is treated with TBAF as described in Step B of Example 2, above, to obtain the corresponding diol-ester (a compound I′) which upon treatment with an equivalent of 1N sodium hydroxide followed by lypholization, yields the title sodium salt product of this example (59 gm), which is characterized as follows:

IR (KBr): 1580, 1508, 1405, 1220, 1160, 1120, 1080, 980, 820, 750 cm$^{-1}$.

EXAMPLE 6

Repeating the procedure of Examples 1 and 2, but in Step A employing in place of the ethyl ester used therein, an approximately equivalent amount of
 (a) n-propyl;
 (b) isopropyl ester; or
 (c) t-butyl ester (as a compound A);
there is accordingly obtained the analogous:
 (a) n-propyl;
 (b) isopropyl; and
 (c) t-butyl esters of the products of Steps A, B, C and D of Example 1 and of Steps A and B of Example 2.

EXAMPLE 7

(E)-Trans-6-(2-phenylethenyl)-4-hydroxy-tetrahydropyran-2-one.

A solution of 91 mg (0.13 mmol) of the di-protected-olefinic product of step A, of Example 2. 0.06 ml (1 mmol) of glacial acetic acid and 1 ml (1 mmol) of 1M TBAF solution in THF, is stirred at room temperature for 18 hours, followed by heating the mixture for 2 hrs. at 80° C. The mixture is diluted with 20 ml of CH₂Cl₂, washed with water, the organic phase separated, dried, evaporated, and the residue chromatographed on silica gel using ethyl acetate as eluant. The title product of this example (14 mg) is isolated, m.p. 94°–95°.

EXAMPLE 8

Repeating the procedure of Example 7, but using in place of the methyl erythro-3,5-di-(diphenyl-t-butyl-siloxy-7-phenyl-hept-6-enoate used therein, an approximately equivalent amount of:
(a) (E)-methyl erythro-3,5-di-(diphenyl-t-butylsiloxy)-7-(2'-[4"-fluorophenyl]-naphth-1-yl)hept-6-enoate; (product of Step A of Example 2); or
(b) (E)-methyl erythro-7-[1'methyl-3'-(4"-fluorophenyl)indol-2'-yl]-3,5-di-(diphenyl-t-butylsiloxy)-hept-6-enoate, (product of Step A of Example 5);
there is accordingly obtained the corresponding compounds I''':
(a) (E)-trans-6-(2'-[2"-(4'''-fluorophenyl)naphth-1"-yl]ethyl)-4-hydroxy-3,4,5,6-tetrahydro-2H-pyran-2-one; and
(b) (E)-trans-6-[1'-methyl-3'-(4"-fluorophenyl)indol-2'-ylethenyl]-3,4,5,6-tetrahydro-4-hydroxy-2H-pyran-2-one, respectively.

EXAMPLE 9

Repeating procedure of Example 1, but in Step A in place of the acrolein used therein, using an approximately equivalent amount of crotonaldehyde, there is accordingly obtained the corresponding products of each of the Steps A, B and C of Example 1 and the same product as of Step D thereof.

What is claimed is:

1. A process for preparing an aldehyde of the formula E:

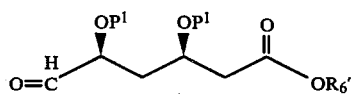

wherein $P^1$ is a protective group which is either (1) a trisubstituted silyl radical having at least 2 bulky radicals selected from the group consisting of (a) tertiary alkyl ($C_4$ to $C_8$) groups and (b) phenyl which may be unsubstituted or substituted by up to 2 of any of lower alkyl ($C_1$–$C_4$), chloro, nitro, trifluoromethyl, or monosubstituted in the para-position by phenyl or benzyl which may be unsubstituted or in turn mono-substituted by one at the para-position by one of such groups as mentioned above, any non-bulky radical being unbranched alkyl having for 1 to 4 carbon atoms; or (2) lower alkyl having from 1 to 4 carbon atoms, and $R_6'$ is alkyl having from 1 to 3 carbon atoms, n-butyl, i-butyl, or t-butyl or benzyl comprising:
(A) reacting a dianion of an ester of aceto-acetic acid of the formula "A":

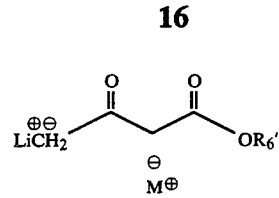

wherein $R_6'$ is as defined, and M is an equivalent of an alkali metal cation, with an aldehyde of the formula J:

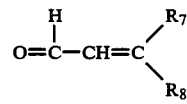

wherein each of $R_7$ and $R_8$ is, independently, hydrogen or alkyl having from 1 to 6 carbon atoms, to form a corresponding ester of hept-6-enoic acid of the formula B:

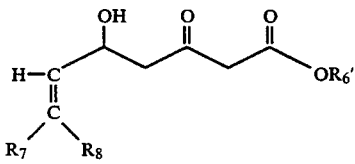

wherein $R_6'$, $R_7$ and $R_8$ are as defined;
(B) reducing said compound of formula B to form a corresponding diol of formula C:

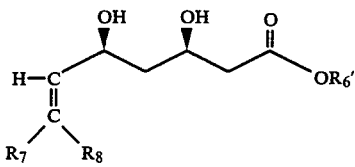

wherein $R_6'$, $R_7$ and $R_8$ are as defined;
(C) etherifying said compound of formula C with a reagent of the formula IV $$P^1-L \qquad\qquad IV$$

wherein $P^1$ is as defined, and L is a leaving group, selected from the group consisting of chloro, bromo, or iodo, and alkyl or phenyl sulfonyl, in which alkyl is $C_1$–$C_6$ and phenyl may be unsubstituted or mono-substituted by a $C_1$–$C_4$ alkyl; to form a corresponding protected olefin of formula D):

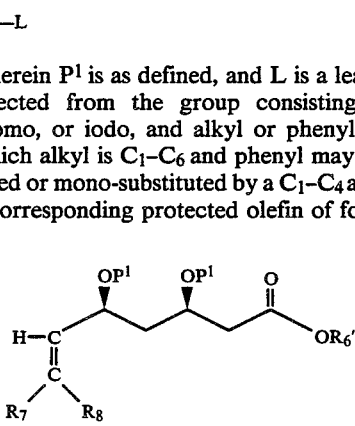

wherein $R_6'$, $R_7$, $R_8$ and $P^1$ are as defined; and D) oxidizing said compound of formula D to form a corresponding compound of formula E, as defined.
2. A compound of formula B as defined in claim 1.
3. A compound of formula C as defined in claim 1.
4. A compound of formula D as defined in claim 1.

5. A process of claim 1 in which the reagent IV is chloro-diphenyl-t-butylsilane.

6. A process of claim 1 in which $P^1$ is diphenyl-t-butylsilyl.

7. A compound of claim 4 in which $P^1$ is is diphenyl-t-butylsilyl.

8. A process of claim 1 in which each of $R_7$ and $R_8$ is a hydrogen atom.

9. A compound of claim 4 in which each of $R_7$ and $R_8$ is a hydrogen atom.

10. A process of claim 1 in which L of reagent IV is chloro.

11. A process of claim 1 in which $R_{6'}$ is methyl.

12. A compound of claim 4 in which $R_{6'}$ is methyl.

13. A compound of claim 4 in which $R_{6'}$ is ethyl.

14. The compound of claim 4 in which $P^1$ is diphenyl-t-butylsilyl; $R_{6'}$ is ethyl, and each of $R_7$ and $R_8$ is hydrogen.

15. A process of claim 1 in which M of compound A'' is lithium.

* * * * *